US011317225B2

(12) United States Patent
Karamuk et al.

(10) Patent No.: US 11,317,225 B2
(45) Date of Patent: Apr. 26, 2022

(54) IN-EAR HOUSING WITH CUSTOMIZED RETENTION

(71) Applicant: Sonova AG, Stäfa (CH)

(72) Inventors: Erdal Karamuk, Männedorf (CH); Jana-Kosima Schwarzlos-Sooprayen, Stäfa (CH); Natasha Thumm, Wetzikon (CH); Andi Vonlanthen, Oberrohrdorf (CH)

(73) Assignee: Sonova AG, Stäfa (CH)

( * ) Notice: Subject to any disclaimer, the term of this patent is extended or adjusted under 35 U.S.C. 154(b) by 149 days.

(21) Appl. No.: 16/641,269

(22) PCT Filed: Aug. 24, 2017

(86) PCT No.: PCT/EP2017/071329
§ 371 (c)(1),
(2) Date: Feb. 24, 2020

(87) PCT Pub. No.: WO2019/037855
PCT Pub. Date: Feb. 28, 2019

(65) Prior Publication Data
US 2020/0186905 A1    Jun. 11, 2020

(51) Int. Cl.
*H04R 25/00* (2006.01)
*A61F 11/08* (2006.01)
*H04R 1/10* (2006.01)

(52) U.S. Cl.
CPC ............ *H04R 25/652* (2013.01); *A61F 11/08* (2013.01); *H04R 1/1016* (2013.01); *H04R 1/1058* (2013.01); *H04R 25/658* (2013.01)

(58) Field of Classification Search
CPC ...... H04R 25/606; H04R 25/00; H04R 25/60; H04R 25/456; H04R 2460/09; H04R 2460/11
See application file for complete search history.

(56) References Cited

U.S. PATENT DOCUMENTS

| 3,934,100 A * | 1/1976 | Harada ............... H04R 25/656 181/135 |
| 2006/0023908 A1* | 2/2006 | Perkins ............... H04R 25/606 381/328 |

(Continued)

FOREIGN PATENT DOCUMENTS

| DE | 102008062844 B3 | 7/2010 |
| DE | 102012015496 A1 | 2/2014 |

(Continued)

OTHER PUBLICATIONS

European Patent Office, International Searching Authority, International Search Report for PCT/EP2017/071329, dated Feb. 28, 2019, Rijswijk, Netherlands.

*Primary Examiner* — Amir H Etesam
(74) *Attorney, Agent, or Firm* — ALG Intellectual Property, LLC

(57) ABSTRACT

A custom fit hearing device that includes an in-ear housing designed to fit at least partially in a hearing device user's ear canal. The in-ear housing includes one or more areas on its outer-surface that are designed to provide retention of the in-ear housing in the ear canal. The one of more area may be rougher than the rest of the outer-surface of the in-ear housing, may have greater a friction coefficient than the rest of the outer-surface of the in-ear housing, may be made of a different material than the rest of the outer-surface of the in-ear housing, may contain granular material and/or may include surface features such as shapes extending outward from the outer-surface or undulations/ripples in the outer-surface. The in-ear housing may be produced using virtual designs and a 3D scan of the ear canal and may be manufactured using additive manufacturing or 3D printing.

18 Claims, 4 Drawing Sheets

(56) References Cited

U.S. PATENT DOCUMENTS

| | | | |
|---|---|---|---|
| 2006/0175722 A1* | 8/2006 | Babcock | B29C 44/0461 |
| | | | 264/41 |
| 2010/0304065 A1 | 12/2010 | Tomantschger et al. | |
| 2013/0034258 A1 | 2/2013 | Lin | |

FOREIGN PATENT DOCUMENTS

| | | |
|---|---|---|
| EP | 2130402 B1 | 5/2013 |
| WO | 2002071794 A1 | 9/2002 |

\* cited by examiner

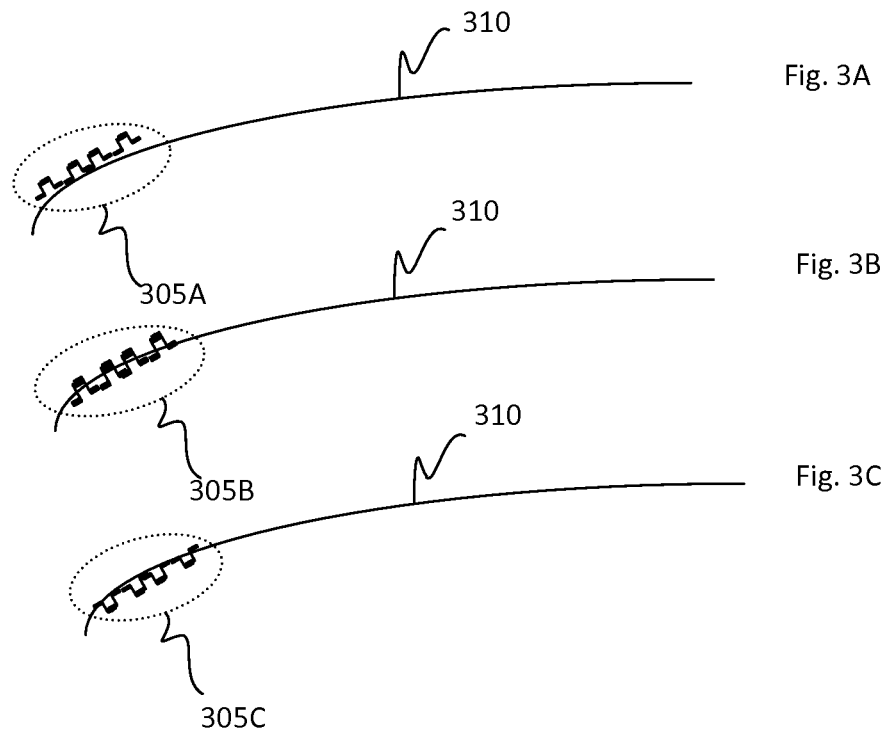
Fig. 3A
Fig. 3B
Fig. 3C
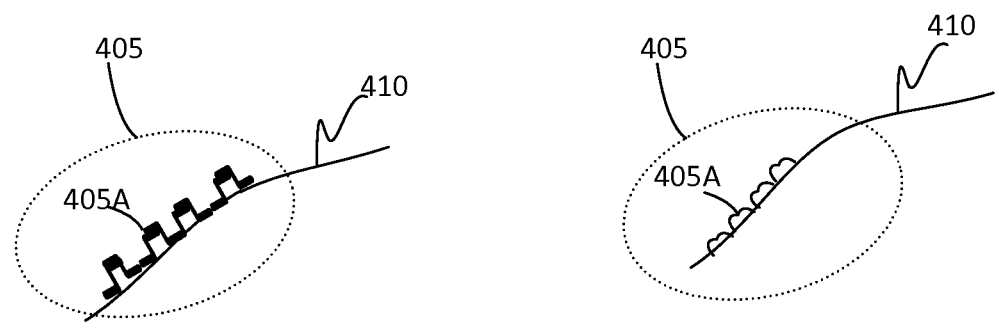
Figure 4A
Figure 4B

IN-EAR HOUSING WITH CUSTOMIZED RETENTION

BACKGROUND

Embodiments of the present disclosure pertain to custom designed earpieces and hearing device housings (commonly referred to as shells) configured to be worn at least partly within a user's ear canal. More particularly, embodiments of the present disclosure concern retention of the hearing device housings/earpieces in the user's ear canal.

Hearing devices may be used to improve the hearing capability or communication capability of a user, for instance by compensating a hearing loss of a hearing-impaired user, in which case the hearing device is commonly referred to as a hearing aid, hearing instrument or hearing prosthesis. A hearing device may also be used to communicate a sound to a user's ear. For example, sound may be communicated to a hearing device, which may reproduce the sound in the user's ear canal.

A hearing device may use a microphone to pick up/receive sound. Circuitry in the hearing device can process signals from the microphone, and provide the processed sound signal into the ear canal of the user via a miniature loudspeaker, commonly referred to as a receiver. Hearing devices may also receive sound signals from alternative input sources, such as an induction coil and/or a wireless transmitter, for example via a mobile phone, wireless streaming and/or the like, and process these sounds signals and deliver them to the user. Furthermore, hearing devices may be employed as hearing protection devices that suppress or at least substantially attenuate loud sounds and noises that could harm or even damage the user's sense of hearing. For purposes of this disclosure, the term hearing device includes earphones or the like that deliver sound to a user's ear canal.

A hearing device comprises a housing. If the hearing device is an in-the-ear hearing device (ITE) it is worn at least partly within the user's ear canal. If the hearing device is a completely-in-canal hearing device (CIC) it is worn entirely within the user's ear canal. Deep fitted CICs are worn within the bony portion of the user's ear canal close to the eardrum. A behind-the-ear hearing device is worn at the outer ear, usually behind the pinna, and comprises an earpiece, which is inserted into the ear canal for acoustically coupling the sound output by the receiver into the ear canal.

Embodiments of the present disclosure are directed to housings for hearing devices and for earpieces that are configured to be worn at least partly within a user's ear canal. For purposes of this disclosure, the term "In-Ear Housing" (IEH) is used to collectively describe a hearing device housing or an earpiece housing, such as an earmold, otoplastic and/or the like.

Custom-shaped IEHs are individually formed to fit into the ear canal of a specific user. ITE and CIC hearing devices may comprise additively manufactured housings, which may be made of metal, acrylic materials, polymers, vinyl and/or the like. After additive manufacturing, a lacquer can be applied to the housing to provide for biocompatibility and/or to enhance visual appearance.

Recently, ITEs and CICs have been manufactured with metal housings, such as titanium, titanium alloys, stainless steel, stainless steel alloys and/or the like. Metal housings manufactured by additive manufacturing generally have a rough surface and a surface treatment(s) is applied to reduce this roughness and achieve surface properties for cosmetic appearance and/or to improve biocompatibility; e.g., by producing surfaces that are biocompatible with the ear canal skin.

ITEs and CICs need to be retained in the user's ear during use. For example, the IEH should provide sufficient retention for the hearing device in situations where the user makes movements of the jaw—in many people, when they open their mouths, the ear canal changes shape allowing for movement of the ITE/CIC—or the head. Retention does not only concern retaining positioning of the hearing device in the user's ear, it also concerns maintaining a seal between the user's ear and an outer-surface of the IEH.

This seal affects the acoustic performance of the hearing device and if the seal is lost, such as by movement of the hearing device in the user's ear, the acoustic performance of the hearing device is impaired.

The problem of providing adequate retention for custom-shaped IEHs is compounded because many different factors contribute to an optimal fit of the ITE/CIC. Such factors for optimal fit/retention, include the curvature of the ear canal, the size and shape of the IEH, the total contact area between the ear canal and the IEH, the radial pressure exerted on the ear canal by the IEH, e.g., the dimensions and/or flexibility of the IEH affect a radial pressure produced by the IEH on the ear canal wall, and/or the like.

Custom IEHs may be manufactured by a computer aided design (CAD) and/or a computer-aided manufacturing (CAM) method in which an impression of the user's ear undergoes digital scanning and virtual modelling. Modelling is a process where a hearing technician modifies a virtual impression with 3D modelling software to create a virtual IEH. The virtual IEH can be modified by the hearing technician to adjust/optimize the model, meet the user's requirements, adjust the model to the material of manufacture of the IEH and/or the like.

Manufacture of metal IEHs has several challenges. For example, in some manufacturing processes, a coating can be applied to a metallic IEH to help control its retention, e.g. the ability/property of the hearing device housing to safely stay in place in the ear canal even during movement of the jaw, the head and/or the like. However, use of a coating can reduce the biocompatibility properties of the metal, cause hypersensitivity for some users and can result in increased costs and reduced precision.

To provide for IEH retention, earmold modelling may be used to design an IEH that is shaped to fit 'snugly' with a portion of a user's inner-ear. Moreover, compliance properties of the IEH, its softness/hardness, may also provide for retention.

SUMMARY

In embodiments of the present disclosure, IEHs are provided that are configured to be worn at least partly within an ear canal of a user, which are shaped according to at least part of the ear canal of the user, and comprise an area of an outer-surface of the IEH that provides a different interaction effect with the ear canal compared with the remainder of the outer-surface of the IEH. The interaction effect may be produced by a roughness and/or a frictional property of the area.

In some embodiments, the IEH of a hearing device is custom designed for the user to have one or more areas on the surface of the IEH to provide for improved retention of the IEH in the user's ear. In some embodiments, the improved retention properties are produced by one or more areas of the outer-surface of the IEH having greater roughness or a greater friction coefficient than the remaining areas of the surface of the IEH.

In some embodiments, location, friction properties and/or the degree of roughness of the one or more areas can be customized to provide for retention in the user's ear, user comfort and ease of insertion/retraction of the hearing device. The custom design may be determined during modelling and can be based on design rules for a given IEH form factor and a given ear canal geometry, modeler experience feedback from audiologists or hearing aid users and/or the like.

In some embodiments, the IEH may comprise a plastic/polymer—such as an acrylic resin, a polyurethane, an acrylic, a vinyl, metal—such as titanium, a titanium alloy, stainless steel, a stainless-steel alloy and/or the like, a silicon/silicon derivative and/or the like. In determining the location, friction properties and/or the degree of roughness of the one or more areas of the IEH, the material of the IEH and/or the material to be used at the one or more areas may be considered in the modelling process.

In some embodiment of the present disclosure, the roughness of at least one area of the outer-surface of the IEH can be greater by an amount in a range from about 50% to 200% compared with other areas of the outer-surface of the IEH.

In some embodiments, a material may be used to manufacture at least one area of the outer-surface of the IEH having a friction coefficient greater by an amount in a range from about 50% to 200% compared with a friction coefficient of other areas of the outer-surface of the IEH.

In some embodiment of the present disclosure, a roughness of at least one area of the outer-surface of the IEH may be increased by incorporating granules of material in the at least one area of the outer-surface of the IEH. The granules may be formed from the same material as the rest of the outer-surface or may comprise a different material, for example a harder material.

In some embodiments of the present disclosure, an arithmetic mean roughness (Ra), (measured per the International Organization for Standardization (IOS) standard DIN EN ISO 4287 for determining surface texture properties) of a roughened area of the outer-surface of the IEH may be in a range from about Ra=0.7 µm to Ra=1.8 µm.

In some embodiments, the outer-surface of the hearing device housing can comprise at least one area comprising surface elements formed on the outer-surface of the IEH. These surface elements may be integral to the IEH and extend outward from the outer-surface, e.g., creating projections on the outer-surface. The surface elements can locally increase the roughness and/or friction coefficient of the hearing device housing at the at least one area of the outer-surface.

In some embodiments, the IEH can be manufactured by additive manufacturing, 3D printing, selected laser sintering, selective laser melting, stereo lithographic apparatus, digital light processing and/or the like. For example, surface elements may be formed on the outer-surface of the IEH using additive manufacturing and/or 3D printing.

In some embodiments, a metallic IEH can be formed by a selective laser melting process of a metal powder. In some embodiments, the IEH is made of a metal and/or a metal alloy, and may be formed by a selective laser melting process of titanium powder.

In some embodiments, the surface properties of the IEH, including an area of increased roughness, can be produced by surface treatment. Surface treatment methods may include: lacquering, surface vibratory grinding, centrifugal disc finishing, abrasive blasting, electropolishing and/or the like. For example, the surface treatment can be applied non-uniformly to the outer-surface to produce an area on the outer-surface with a desired elevated roughness with respect to a remainder/portion of a remainder of the outer-surface. In some embodiments, the IEH comprises the area of elevated roughness prior to surface treatment and the properties of the area are selected to provide the desired roughness effects after surface treatment.

Some embodiments provide a method of manufacturing a hearing device comprising an IEH with a section of an outer-surface of the IEH, which may be configured to contact a wall of an inner-ear/ear canal, that has increased roughness/friction properties compared to other sections of the outer-surface of the IEH. In some embodiments for manufacturing the IEH, a three-dimensional (3D) model of the IEH may be produced by 3D modelling software based on a measured shape of at least part of the ear canal of the user; the model may be analysed to determine/measure a level of retention of the hearing device housing within the ear canal of the user and to determining a location, roughness and/or friction properties of at least one area of an outer-surface of the IEH to produce an improved/desired retention.

In some embodiments, the retention properties of the location, roughness and/or friction properties of the at least one area is balanced against user comfort properties of the proposed IEH and/or insertion/retraction properties of the proposed IEH. In some embodiments, virtual interpretation and/or user input (such as the user testing a prototype IEH) are used to determine the location, roughness and/or friction properties.

In some embodiments, different types of surface roughness and/or friction properties may be evaluated in the 3D model. In some embodiments, the surface roughness is provided by surface elements to be provided in an area of the outer-surface of the IEH. The roughness/friction effects of the surface elements may depend upon: a height/depth of the surface elements with respect to the outer-surface of the IEH, the shape of the surface elements, the geometrical distribution of the surface elements on the outer-surface of the IEH, interaction of the surface elements with the ear-canal wall and/or the like. As such, in some embodiments of the present disclosure, retention properties of a virtual model of the IEH may be determined by modelling retention properties of different surface elements and/or different locations of surface elements.

In some embodiments, the surface elements comprise at least one of the following:

elongated structures, such as ridges, troughs; notches; dykes; ducts; grooves; wavelike structures, pointed ridges (e.g., triangular type ridges or troughs) and/or the like;

protrusions and/or depressions, such as knobs, studs, pimples, potholes, pockets, pyramids, hooks, spherical protrusions/depressions, quadrilateral protrusions/depressions and or the like.

In some embodiments of the present disclosure, a height or depth of the surface elements with respect to the outer-surface of the IEH in which the surface elements are formed and/or the separation of surface elements may be of the order of 10s or 100s of micro-meters. For example, in some instances, height/depth of the surface elements and/or separation of the surface elements can be in the range from about 50 µm to 500 µm.

In some embodiments, the surface elements can: protrude outwardly from the surface of the IEH; protrude inwardly into the surface of the IEH; or protrude partly outwardly from the surface of the IEH and partly inwardly into the surface of the IEH.

In some embodiments, the surface elements may be configured to form a regular pattern on the surface of the IEH. For example, in some embodiments, the surface elements may be arranged in parallel geometries, may be arranged circumferentially around an axis (a central line or point), may extend from a distal end of the IEH to a proximal end of the IEH, maybe arranged to form a mesh, web or grid, may form a spiral-type pattern and/or the like In some embodiments of the present disclosure, a roughened area, e.g. an area of increased roughness is applied to a surface of an IEH. Application of the roughened area may be made by any method that increases the roughness of an area of the IEH surface. However, precision methods— where a size of the roughened area, a location of the roughened area on the surface, the roughness of the area, the shape of the surface elements, the size of the surface elements, the distribution of the surface elements and/or the like can be controlled—provide for better retention, customer comfort, insertion/removal, reproducibility of the results of the 3D modelling and/or the like.

In some embodiments, methods for creating the roughened area may include: additive manufacturing, such as 3D printing, stereolithography, laser sintering and/or the like; laser surface treatments, such as selective laser melting, laser etching and/or the like; chemical etching and/or the like.

Further embodiments of the present disclosure provide that the retention to be provided by the IEH with a roughened area/increased friction properties can be based on feedback provided by an individual user regarding at least one of a level/measure of retention, insertability, extractability and wearing comfort. This input may be provided based upon feedback from a user regarding experiences wearing an evaluation hearing device or of a previously worn IEH.

In some embodiments, the modelling software may analyse a proposed earmold for the IEH and determine the properties for a roughened area and/or an area with a high friction coefficient to be provided on the IEH. This analysis and determination of properties of the roughened area may comprise using design rules for different types of IEHs, such as (partly-) in-the-ear (ITE), completely-in-canal (CIC) and deep-fitted IEHs.

These and further objects, features and advantages of the present invention will become apparent from the following description when taken in connection with the accompanying drawings which, for purposes of illustration only, show several embodiments in accordance with the present disclosure.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIGS. 3A-C illustrate different offsets of surface features configured to increase surface roughness of an area of an outer-surface of an in-ear housing, in accordance with some embodiments of the present disclosure.

FIGS. 4A and 4B illustrate effects of surface treatments on surface features of an in-ear housing, in accordance with some embodiments of the present disclosure.

Figure 1A:
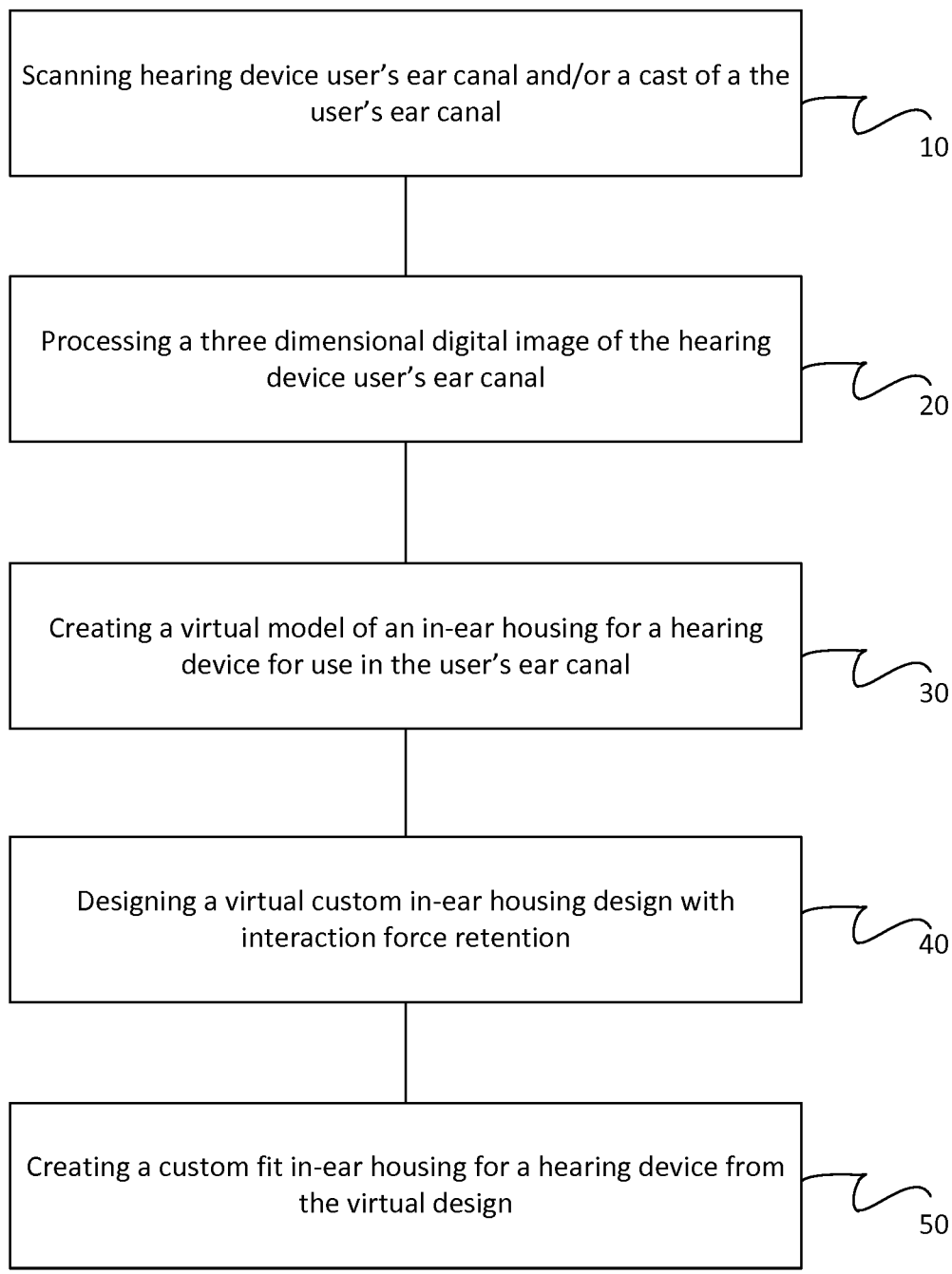
FIG. 1A illustrates a method for producing a custom in-ear housing for a hearing device having varied surface roughness to provide for in-ear retention, in accordance with some embodiments of the present disclosure.

These and further objects, features and advantages of the present invention will become apparent from the following description when taken in connection with the accompanying drawings which, for purposes of illustration only, show several embodiments in accordance with the present disclosure.

DESCRIPTION

The ensuing description provides some embodiment(s) of the invention, and is not intended to limit the scope, applicability or configuration of the invention or inventions. Various changes may be made in the function and arrangement of elements without departing from the scope of the invention as set forth herein. Some embodiments maybe practiced without all the specific details. For example, circuits may be shown in block diagrams in order not to obscure the embodiments in unnecessary detail. In other instances, well-known circuits, processes, algorithms, structures and techniques may be shown without unnecessary detail in order to avoid obscuring the embodiments.

Some embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure and may start or end at any step or block. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded or transmitted via any suitable means including memory sharing, message passing, token passing, network transmission, etc.

The phrases "in some implementations," "according to some implementations," "in the implementations shown," "in other implementations," and generally mean the particular feature, structure, or characteristic following the phrase is included in at least one implementation of the disclosed technology, and may be included in more than one implementation. In addition, such phrases do not necessarily refer to the same embodiments or different implementations.

Reference will now be made in detail to embodiments, examples of which are illustrated in the accompanying drawings and figures. In the following detailed description, numerous specific details are set forth in order to provide a thorough understanding of the subject matter herein. However, it will be apparent to one of ordinary skill in the art that the subject matter may be practiced without these specific details. In other instances, well known methods, procedures, components, and systems have not been described in detail so as not to unnecessarily obscure features of the embodiments. In the following description, it should be understood that features of one embodiment may be used in combination with features from another embodiment where the features of the different embodiment are not incompatible.

Hearing devices include hearing instruments—such as behind-the-ear hearing aids, in-the-ear hearing aids etc.—earphones, in-ear headphones, noise protection systems worn on/in the ear that include a speaker, and/or the like.

Custom made hearing devices/earpieces worn at least partly within a user's ear canal are designed in part to provide for creating a seal between the hearing device and the ear canal. This seal prevents unwanted acoustic effects that are detrimental to the operation of the hearing device. As such, the custom hearing device needs to retain its position in the ear canal of a user providing the seal with the ear canal, while the user goes about his/her daily life. However, means for retention of the hearing device in the ear canal need to be balanced against the user's comfort wearing the hearing device and ease of inserting/removing the hearing device.

Custom hearing devices are made from an impression taken from the user's ear canal. The impression may comprise an earmold taken from the ear canal, a scan of the ear canal and/or the like. In some instances, a mould is taken of the ear canal and a 3D scan is formed of the mould to provide a virtual image of the ear canal.

A clinician/person fitting the hearing device evaluates the ear impression/scan prior to manufacture of the custom hearing device. The clinician may determine what IEH is best suited for the user's ear. Custom IEHs need to have the best possible fit in the patient's ear. In some instances, custom IEHs are made from ear impressions individually taken from the patient, and ideally carry many of the ear's unique features.

Retention in the context of custom made IEHs is the ability of the IEH to safely stay in place—in the ear canal of a user—even through movements of the jaw or the head.

Achieving adequate retention can be challenging in custom made IEHs since different factors contribute to an optimal fit.

Previously, the fitting factors that have been considered have focusing mainly on the curvature of the ear canal and the IEH, and the existence of undercuts and retention areas.

In embodiments of this disclosure, surface roughness/friction properties of the IEH, and in particular the use of one or more areas of surface roughness having higher roughness properties than the rest of the surface of the IEH are used to improve retention properties of the IEH.

Post processing of manufactured IEHs may include subsequent surface finishing techniques such as vibratory grinding and sand blasting. Those processes are intended to transform the initially rough surface of the IEH, which may be particularly rough for metal IEHs made by an SLM process or the like, into a smoother surface that is closer to the topographic properties of human skin, and thus more comfortable to be worn in the ear. The final surface topology of the IEH may thus be determined by the various processing parameters such as grinding agents, polishing agents, time, rotational speed etc. Generally, these processes act globally on the IEH as most of the steps are performed in batch processes for optimization of manufacturing cost and throughput.

United States Patent Pub. No. 2007081685 describes textured surfaces for hearing aids. While an increased surface roughness may be beneficial for good retention and sealing in the ear canal, a roughness that is too great makes it difficult for the user to insert the hearing device/earpiece into the ear and may adversely affect the desired properties of the hearing device/earpiece.

In accordance with some embodiments of the present disclosure, by controlling the surface roughness/dynamic friction parameter of a selected location(s) of the outer-surface of the IEH, comfort and retention may be provided in parallel, providing for selective surface roughness in dedicated areas of the IEH where it will not, or will only partially interfere with the ease of insertion or removal of the IEH.

In some embodiments of the present disclosure, non-uniform surface finishing of the IEH can be produced, amongst other ways by:
manual process where operators using hand-tools prepare the surface of the IEH by generating non-uniform surface roughness by polishing certain areas of the shell more than others or by roughening some areas;
batch-processing where some areas that need to have different surface properties are manually masked during certain processes in order to achieve a non-uniform surface roughness in the final IEH;
batch processing where the area(s) selected to have different surface properties are produced by additive manufacturing/3D printing and are configured to produce a desired roughness after the batch-processing; and
chemical deposition/degradation where masking is used with chemicals to deposit/etch material from areas of the outer-surface of the IEH.

FIG. 1A illustrates a method for producing a custom in-ear housing for a hearing device having varied surface roughness/friction properties to provide for in-ear retention, in accordance with some embodiments of the present disclosure.

In 10, to produce a custom-fit IEH for a hearing device an impression of a hearing device user's ear canal can be scanned. In some embodiments, a direct scan may be made of the user's ear canal. In the former method, an impression of the user's ear canal is cast/moulded and placed in a laser scanner. The laser scanner creates digital images of the cast and transmits them to processing circuitry.

In 20, the processing circuitry constructs a three-dimensional image of the user's ear canal. The processing circuitry and/or an operator may edit the 3D image to account for features in the cast/scan, such as sharp edges, agglomeration of moulding material, obvious defects in the scan and/or the like.

In 30, the 3D digital image of the ear canal is used to process a virtual model of a custom in-ear housing to fit the user's ear canal. In 30, a shape of the virtual model of the IEH can be processed to conform with at least a part of the 3D digital image of the ear canal. In some embodiments of the present disclosure, areas of contact and/or heightened contact between the virtual model of the IEH and the ear canal (as determined from the ear canal scan) can be identified. Moreover, in some embodiments, physical properties of the contact between the virtual IEH and the user's ear canal can be processed. For example, the physical properties may be processed from: frictional properties of the proposed IEH material and/or the ear canal; tightness of fit of the virtual IEH at the contact location; geometry of the virtual IEH and/or the ear canal at the contact point and/or the like.

Virtual modelling of the custom IEH may be precisely controlled with an operator able to select a thickness of an impression coating, called an "offset surface." For example, modelling software may provide a 0.3 mm offset surface that is applied to the virtual IEH and means that the IEH will be 0.6 mm (0.3+0.3 mm) tighter in the ear than the impression taken of the ear canal.

In 40, in accordance with embodiments of the present disclosure, contact areas where the virtual IEH contacts the ear canal and/or has heightened contact with the ear canal may be selected as locations for providing one or more areas of increased interaction forces between the IEH and the ear canal on the IEH to provide for retention of the IEH in the ear canal.

The tightness of fit of the IEH may vary at different locations of the IEH depending upon the shape of the ear canal and/or the shape of the IEH. Using the digital image of the ear canal and the virtual model of the IEH, the radial pressure exerted by the IEH may be processed. In embodiments of the present disclosure, a radial pressure map may be processed for an outer-surface of the IEH of the variations of radial pressure and this may be used to identify the areas of heightened contact between the IEH model and the ear canal.

Increased interaction forces between the IEH and the ear canal may be provided in some embodiments by increasing the roughness/texture of the one or more selected areas, providing granules of material at the one or more selected areas and/or using materials with high friction coefficients at the one or more selected areas. Providing locations on a surface of the IEH to have increased roughness/texture/friction properties to provide for retention of the IEH may be referred to as roughness retention.

In some embodiments, based upon characteristics of a contact between the IEH and the ear canal—such as geometry of the IEH/ear canal, fit of the IEH and the ear canal (loose or tight fit), orientation of the IEH and/or the like—areas of a surface of the IEH may be selected to have increased interaction forces with the ear canal. For example, the one or more selected areas may be configured to have increased roughness/texture with respect to the other areas of the surface of the IEH. In some embodiments, multiple areas may be identified to have increased interaction forces. The radial pressure variations produced by the virtual model of the IEH may be used to select the areas to have increased roughness/friction properties and/or an amount of increased roughness/friction properties.

In processing selection of multiple areas to have increased interaction forces, a combined effect of the selected areas may be processed and proposed locations may be varied to optimize friction/roughness retention provided by the multiple selected areas. Processing selection of one or more areas on the IEH outer-surface to have increased interaction forces to provide for roughness retention may comprise processing effects of the variable roughness/friction properties of the outer-surface of the IEH on ease of insertion/removal of the IEH into/from the ear canal. As such, in some embodiments, a model of one or more variable roughness areas on the outer-surface may be optimized for roughness retention and ease of insertion and/or removal.

In some embodiments of the present disclosure, roughness parameters/friction parameters for a selected contact area may be modelled using the virtual IEH, the ear canal image and/or the physical properties of the selected contact area (properties of the IEH and/or the ear canal at the selected contact area). For example, different configurations of surface features to be provided at the one or more areas having greater roughness/texture may be applied to the virtual IEH and the interaction with the ear canal modelled. Surface features may comprise: three dimensional shapes, undulations in the surface, grid like structures, granular shapes, variations in materials forming the rougher surface (such as materials with different dynamic friction properties) and/or the like.

In some embodiments, materials with high friction coefficients may be integrated into an area of the outer-surface to increase the friction between the area and the ear canal increasing retention. The area may be integrated in the outer-surface by changing the material used in the additive manufacturing for the area in contrast to material used in additive manufacturing of the rest of the outer-surface. Materials may have different friction coefficients and some materials may have an inherent "tackiness" and/or adhesive like property. In some embodiments, areas with both different friction properties and roughness may be used for the IEH. In some embodiments, one or more areas of material with high a high friction coefficient may be used with one or more areas with high roughness.

In 40, different surface features can be applied to different locations of the outer-surface of the IEH and the interaction between the surface features at the different locations and the overall effects produced may be modelled so that locations and surface features producing desired/optimized retention effects can be incorporated in the virtual IEH design.

In some embodiments, the IEH design includes addition of local features to the outer-surface of the IEH. These features provide a greater roughness than that provided by the outer-surface of the IEH. Similarly, in some embodiments, the IEH design may include provision of granular substances in a determined area(s) of the outer-surface of the IEH and/or provision of a material(s) having a higher friction coefficient than the rest of the outer-surface of the IEH.

Selection of the area(s) to provide the roughness, granularity and/or higher friction properties can be determined during the modelling process. For example, modelling software may determines the area(s) and/or an operator/hearing device fitter may make a determination of location/properties of surface features. The determination of location/properties of surface features may be based on experience, past performance of custom IEHs, modelling, experimentation and/or defined design rules that might be different for each type IEH.

In some instances, the design of the virtual IEH may comprise: determining areas of the outer-surface of the IEH that provide inherent retention, e.g. through undercuts and/or the like; determining areas of the outer-surface of the IEH that need to be smooth/have low friction properties to facilitate easy insertion and removal of the IEH; identifying areas of the outer-surface of the IEH where additional retention is beneficial; and adding local surface structures/materials onto the beneficial areas to locally increase surface retention properties.

In 50, the virtual design of the IEH with outer-surface features/increased roughness/friction properties for improved retention is used to produce a custom fit in-ear housing. For example, measurements from the virtual design, locations of surface areas having different interaction properties and/or properties of surface features at the location are used as instructions for manufacturing the custom IEH. In some embodiments of the present disclosure, the IEH is produced by additive manufacturing, 3D printing and/or the like.

In 50, the custom IEH may in some embodiments may be produced by Selected Laser Sintering (SLS), Selective Laser Melting (SLM), Stereo Lithographic Apparatus (SLA), and Digital Light Processing (DLP).

In some embodiments using 3D printing/SLA/DLP, the custom IEH may be produced using an acrylic resin that solidifies rapidly when exposed to light. In such embodiments, a laser/ultraviolet light source may be used to build the IEH layer by layer and to produce the desired surface features at selected locations on the outer-surface of the IEH. In embodiments where the custom IEH is produced by 3D printing, there may be no need for buffing and/or polishing the produced custom IEH. In such embodiments, the exact surface features may be constructed on the outer-surface of the IEH, with no need to take account of effects of buffing/polishing the produced custom IEH.

In the SLS/SLM process, the IEH may be made from a polymer powder, such as nylon or the like, or a metal powder, such as titanium or the like. The SLS process produces IEHs that have a textured surface. As a result, the produced IEH needs to undergo surface treatment, such as buffering and/or polishing after manufacture.

In embodiments of the present disclosure using SLS/SLM or the like for the IEH manufacture, the effect of the surface treatment is taken into account in designing the virtual custom IEH and the surface features of the design intended to provide for retention.

In some embodiments, a prototype IEH may be manufactured in 50. The prototype may use inexpensive materials or materials configured for efficient manufacture of a prototype IEH. The prototype IEH may be provided to the user and user input may be fed into the virtual model produced in 30 before manufacture of the final custom IEH.

Figure 1B:
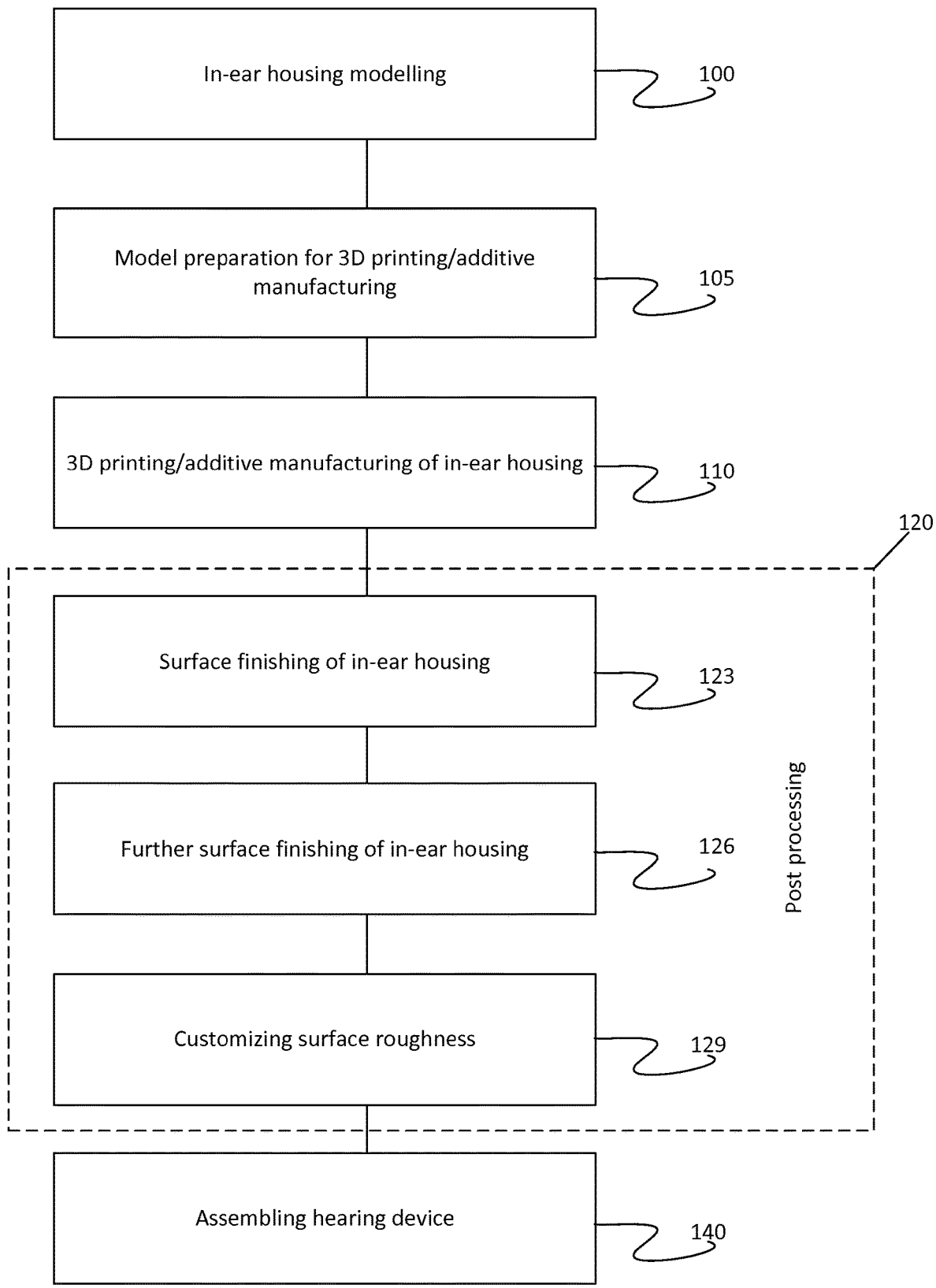
FIG. 1B describes a method for manufacturing a custom in-ear housing with variable outer-surface properties to provide for retention of the in-ear housing, according to some embodiments of the present disclosure.

FIG. 1B describes a method for manufacturing a custom in-ear housing with variable outer-surface properties to provide for retention of the in-ear housing. In some embodiments of the present disclosure the method of manufacturing may comprise additive manufacturing and/or 3D printing. The manufacturing techniques may include surface treatment of the manufactured IEH.

Custom-made shells for ITE and CIC hearing devices as well as earpieces for BTE and RIC (receiver-in-canal) hearing devices are increasingly being manufactured from metal powder, e.g. titanium powder, using selective laser melting (SLM) technology.

A method for manufacturing a custom IEH with one or more areas of increased roughness using SLM is described in FIG. 1B.

As described with respect to FIG. 1A, modelling may be used in 100 to produce a virtual design of the IEH.

In 105, the IEH model is adjusted, as necessary, to provide for use in 3D printing/additive manufacturing of the IEH. For example, measurements and/or the like may be taken from the virtual model and the design may be adjusted to account for effects produced by the 3D printing/additive manufacturing process.

In 110, the IEH can be produced by 3D printing/additive manufacturing based upon the adjusted virtual model of the IEH. In some embodiments of the present invention, the 3D printing/additive manufacturing can be controlled to produce an IEH comprising an outer-surface having one or more areas having increased roughness/friction properties. In some embodiments, the 3D printing/additive manufacturing process may be controlled to provide materials having different roughness/friction properties at one or more areas on the outer surface of the IEH. In some embodiments, the 3D printing/additive manufacturing may produce granulation at one or more areas on the outer surface of the IEH.

The surface of a printed SLM titanium shell is usually very rough, and it is even possible to see single spherical titanium particles of approximately 30 μm diameter that are attached to the shell surface.

In 120, post-processing techniques comprising different surface-treatments can be applied to even the surface structure and/or achieve a visual/cosmetically pleasing surface quality of the manufactured IEH. Surface roughness can also be reduced to improve user comfort, insertion, removal and/or the like.

In 123, in some embodiments, residual powder may be removed from the IEH and the IEH may be subjected to a first surface-treatment. The surface treatment may be performed in a batch process, such as centrifugal disc finishing or the like. Batch processing may be used for surface treatment as it provides for decreased production time, reduces production costs and/or the like.

In some embodiments, further surface processing 126 may comprise polishing the IEH. for a certain amount of time and using a certain type of polishing agent/particle. In some embodiments, abrasive blasting may be used to polish the IEH.

In 129, the surface roughness of the IEH can be customized. Laser engraving, chemical etching and/or the like may be used to produce one or more areas of increased roughness on the IEH.

In 140, a hearing device/earpiece can be assembled using the custom made IEH. Assembly can include integrating electroacoustic, electronic and mechanical components (e.g. microphone(s), receiver, signal processor and volume/program control button(s)) into the hearing device. In between different steps, the IEH can be cleaned using a special cleaning procedure to remove residues of the respective post-processing.

Figure 2:
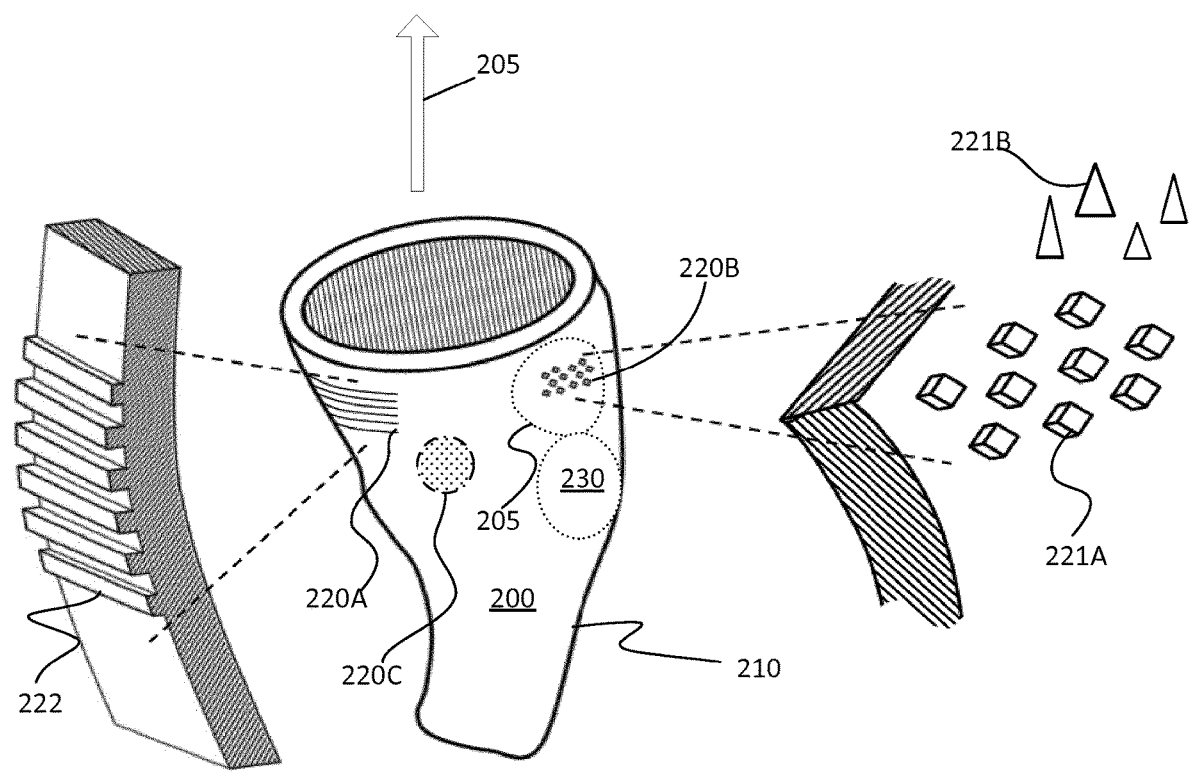
FIG. 2 illustrates examples of contact areas of an outer-surface of an in-ear hearing device having increased roughness/friction properties, in accordance with some embodiments of the present disclosure.

For metal IEHs manufactured according to the method described in FIG. 2, the surface finishing processes can be applied globally to the IEH. In some embodiments of the present disclosure, surface structures/surface materials are applied to one or more areas of an outer-surface of the IEH during the 3D printing/additive manufacturing of the IEH. Modelling of the effects of post processing on the surface structures/surface materials is used so that the surface structures/surface materials created by the 3D printing/additive manufacturing provide the desired retention effects after post processing. For example, in some embodiments of the present disclosure, properties of the surface structures/surface materials—such as size, geometry, depth below the outer-surface, height above the outer-surface, granularity of structures, friction properties and/or the like—produced by the 3D printing/additive manufacturing are configured to account for effects of post-processing on the properties.

FIG. 2 illustrates examples of modified areas of an outer-surface of an in-ear housing for a hearing device, in accordance with some embodiments of the present disclosure. FIG. 2 illustrates examples of an area(s) of an outer-surface 210 of an IEH 200 configured in use to at least partially contact an ear canal of a user of the hearing device. Because the area(s) is configured in use to at least partially contact the ear canal, the area(s) may be referred to in this disclosure as a contact area(s). A remainder of the outer-surface 210 comprises the outer-surface 210 except for the contact area(s).

By way of example, FIG. 2 illustrates three (3) contact area(s) 220A, 220B and 220C that are each configured to have increased/greater roughness and/or friction properties with respect to at least a portion of the remainder of the outer-surface 210, for example a further area 230 of the remainder of the outer-surface 210. The further area 230 may comprise an area surrounding the contact areas 220A, 220B and 220C, may comprise an area appurtenant to the contact areas 220A, 220B and 220C may comprise all of the outer-surface 210 except the contact area(s) and/or the like. The contact areas 220A, 220B and 220C may have increased/greater friction properties (such as a higher friction coefficient with respect to friction between the contact area and the ear canal) than the further area 230, where a friction coefficient for the contact area is greater than a friction coefficient for the further area 230 providing that the contact area exhibits greater frictional force than the further area 230 when the contact area is moved over a surface of the ear canal.

In FIG. 2, the contact area 220A of the outer-surface 210 of an IEH 200 comprises a plurality of ridges 222. In use, the ridges 222 increase the local roughness of the outer-surface 210 and provide for retention of the IEH 200 when contacted with the ear canal (not shown). The location of the ridges 222, the geometry of the ridges 222 and/or physical properties of the ridges 222 may be determined by modelling. In some embodiments, a thickness of the IEH 200 can be approximately 200 µm, the ridges 222 can have a height and width of approximately 50 µm. In some embodiments, after manufacture/post-processing the ridges 222 may not be visible, but may provide a local increase of surface roughness at the first area 220A.

In FIG. 2, the contact area 220B of the outer-surface 210 of an IEH 200 comprises a plurality of surface structures 221A and 221B. The depicted surface structures 221A and 221B are merely intended as examples of structures and any structure that extends outward from the outer-surface 210 may be used. In use, the surface structures 221A and 221B increase the local roughness of the outer-surface 210 and provide for retention of the IEH 200 when contacted with the ear canal (not shown).

The location of the surface structures 221A and 221B, the geometry of the surface structures 221A and 221B and/or physical properties of the surface structures 221A and 221B may be determined by modelling. In some embodiments, the surface structures 221A and 221B may have height and width dimensions of approximately 50 µm. The density of the surface structures 221A and 221B and their placement on the IEH 200 determines an amount of a local increase of surface roughness at the contact area 220B. The surface structures 221A and 221B, in some instances may comprise granular material(s) that is integrated into the outer-surface 210 during additive manufacturing/3D printing of the IEH 200.

In some instances, the surface structures 221A and 221B, the geometry of the surface structures 221A and 221B and/or physical properties of the surface structures 221A are configured to provide that the IEH 200 is less resistant to insertion into the ear canal than to removal from the ear canal. For example, this may be achieved by orienting the surface structures 221A and 221B and/or shaping the surface structures 221A and 221B such that the surface structures 221A and 221B undergo less contact resistance/kinetic resistance with the ear canal during insertion than during removal.

IEHs can be inserted into the ear by inserting and rotating the IEH in the ear canal. This insertion process, in some instance may be modelled, and surface features for the contact areas of the IEH designed to provide for comfortable insertion. Surface features with a spiral arrangement, or with a diagonal arrangement with respect to a longitudinal axis 205 of the IEH may provide for limited resistance to rotational insertion of the IEH, prove greater retention resistance to the IEH moving in the ear canal. For example, ridges 222 in FIG. 2 are aligned normal to the longitudinal axis 205, which mat provide optimal retention properties, but the ridges 222 may be aligned in a diagonal or curved arrangement with respect to the longitudinal axis 205 to balance ease of insertion with retention properties. In such embodiments, the IEH 200 can be comfortably inserted, but provide for good in-ear retention. The modelling process may be used to optimize a balance between comfort of removal of the IEH 200 and retention properties of the IEH 200.

In some instances, the surface structures 221A and 221B can be produced by added manufacturing/3D printing, such as SLM. These processes provide for control of the properties of the surface structures 221A and 221B. From modelling interaction between the IEH and the ear canal desired properties of the surface structures 221A and 221B may be determined. From modelling or the like of effects on the outer-surface of a surface treatment to be applied to the IEH, the additive manufacturing/3D printing may be controlled to produce the surface structures 221A and 221B with physical properties that will produce the desired properties after surface treatment.

Merely by way of example, sharp edged features may be created by the additive manufacturing/3D printing process with the understanding the sharp edges will be blunted by surface treating. Similarly, the surface structures 221A and 221B may be produced by the additive manufacturing/3D printing process with an amount of projection from the outer-surface 210 that will be reduced to a desired projection amount by the surface treating.

In FIG. 2, the contact area 220C of the outer-surface 210 of an IEH 200 comprises a material having a higher friction coefficient that the rest of the outer-surface 210. In use, the material provides increased friction effects between the contact area 220C and the ear canal (not shown). The location of the contact area 220C and the choice of material may be determined by modelling. The material the contact area 220C can be integrated into the outer-surface 210 at a location of the contact area 220C during additive manufacturing/3D printing of the IEH 200.

FIGS. 3A-C illustrate different offsets of surface features configured to increase surface roughness of an area of an outer-surface of an in-ear housing.

Retention of the IEH in the ear canal is determined, at least in part, by an offset parameter with respect to the outer-surface 210 and the ear canal. The amount of offset determines an amount of compression of the ear canal tissue.

FIG. 3A illustrates surface elements 305A protruding outward from an outer-surface 310 of an in-ear housing.

FIG. 3B illustrates surface elements 305B protruding both inward and outward from an outer-surface 310 of an in-ear housing.

FIG. 3C illustrates surface elements 305C protruding inward from an outer-surface 310 of an in-ear housing.

The geometries provided in FIGS. 3A-C produce both different amounts of surface roughness and different offset effects. In the designing of the virtual IEH, both the offset effects of surface features and the offset effect of the surface features at the given area may be modelled to determine the design of the virtual IEH.

FIGS. 4A and 4B illustrate the effects of surface treatment on an IEH manufactured with roughened contact areas, in accordance with some embodiments of the present disclosure.

FIG. 4A, illustrates an outer-surface 410 of an IEH after manufacturing, where the manufacturing can be by additive manufacturing, 3D printing, SLM and/or the like. A contact area 405 formed during the manufacturing process comprises surface features 405A. The surface features, in some instances, may be manufactured with pronounced features and/or sharp edges.

FIG. 4B illustrates the surface features 405A after the manufactured IEH has undergone surface treatment. The surface features 405A after surface treatment may have less pronounced features and/or smoother edges. In some embodiments, the surface features 405A created in the manufacturing process are designed to provide desired properties after the surface treatment process. In this way, in some embodiments, batch surface treatment processing can be used to produce IEHs with an outer-surface comprising contact areas with desired roughness properties.

While the principles of the disclosure have been described above in connection with specific apparatuses and methods, it is to be clearly understood that this description is made only by way of example and not as limitation on the scope of the invention.

What is claimed is:

1. An in-ear housing configured for at least partial insertion into an ear canal of a user of a hearing device, the in-ear housing comprising:
   an outer-surface having a shape based upon at least a part of the ear canal of the user and comprising a plurality of contact areas configured to at least partially contact the ear canal of the user,
   wherein:
      contact areas included in the plurality of contact areas are configured to provide the outer-surface with at least one of varying roughness and varying friction properties, and
      the plurality of contact areas comprises a first contact area having a first texture pattern and a second contact area having a second texture pattern that is different than the first texture pattern.

2. The in-ear housing according to claim 1, wherein a location of the plurality of contact areas and/or an amount of increased roughness and/or varying friction properties with respect to at least a part of a remainder of the outer-surface is selected to improve retention of the in-ear housing in the ear canal.

3. The in-ear housing according to claim 1, wherein a location of the plurality of contact areas and/or an amount of increased roughness and/or the varying friction properties with respect to at least a part of a remainder of the outer-surface is selected to reduce adverse effects of the increased roughness and/or the varying friction properties on inserting or removing the in-ear housing.

4. The in-ear housing according to claim 2, wherein the location of the plurality of contact areas and/or an amount of the increased roughness and/or the varying friction properties with respect to at least a part of a remainder of the outer-surface is selected based upon a radial pressure at the plurality of contact areas.

5. The in-ear housing according to claim 4, wherein a contact area included in the plurality of contact areas is located at a location where the in-ear housing is configured to produce an increased radial pressure on the ear canal with respect to the at least a part of the remainder of the outer-surface.

6. The in-ear housing according to claim 5, wherein a roughness of the contact area is greater by an amount in a range from about 50% to 200% compared with a roughness of the at least a part of the remainder of the outer-surface.

7. An in-ear housing configured for at least partial insertion into an ear canal of a user of a hearing device, the in-ear housing comprising:
   an outer-surface having a shape based upon at least a part of the ear canal of the user and comprising a contact area configured to at least partially contact the ear canal of the user, wherein:
      the contact area comprises at least one of increased roughness and increased friction properties with respect to at least a part of a remainder of the outer-surface;
      a location of the contact area and/or an amount of the increased roughness and/or increased friction properties with respect to the at least a part of the remainder of the outer-surface is selected to improve retention of the in-ear housing in the ear canal;
      the location of the contact area is positioned where the in-ear housing is configured to produce an increased radial pressure on the ear canal with respect to the at least a part of the remainder of the outer-surface;
      the location of the contact area and/or an amount of the increased roughness and/or increased friction properties with respect to the at least a part of the remainder of the outer-surface is selected based upon a radial pressure at the contact area;
      a roughness of the contact area is greater by an amount in a range from about 50% to 200% compared with a roughness of the at least a part of the remainder of the outer-surface; and
      an arithmetic mean roughness (Ra) according to DIN EN ISO 4287 of the contact area is in a range from about Ra=0.7 µm to Ra=1.8 µm.

8. The in-ear housing according to claim 7, wherein the in-ear housing is made of at least one of: a metal, a vinyl, a resin, a silicon, or a plastic.

9. The in-ear housing according to claim 8, wherein the in-ear housing is made of at least on of titanium, cobalt, chrome, or stainless steel.

10. The in-ear housing according to claim 5, wherein the contact area comprises at least one of: a plurality of surface features extending outward from the outer-surface, a plurality of undulations in the outer-surface, or a plurality of granularities on the outer-surface.

11. The in-ear housing according to claim 10, wherein the contact area comprises a material having an increased friction coefficient compared to the at least a part of the remainder of the outer-surface.

12. A method for designing an in-ear housing, the method comprising:
   creating a digital model of an ear canal;
   using the digital model to process a virtual model of the in-ear housing; and
   using at least one of the digital model or the virtual model to design properties of a plurality of contact areas, the plurality of contact areas comprising a first contact area and a second contact area,
   wherein:
      the designing of the properties of the plurality of contact areas comprises designing a first texture pattern of the first contact area and a second texture pattern of the second contact area;
      the second texture pattern is different than the first texture pattern; and
      the designing of the properties of the plurality of contact areas further comprises at least one of:
         designing a location of each of the plurality of contact areas;
         designing a roughness of each of the plurality of contact areas;
         designing surface features for inclusion in each of the plurality of contact areas;
         selecting a contact material of each of the plurality of contact areas;
         selecting a friction property or friction coefficient of each of the plurality of contact areas; or
         designing granulation properties of each of the plurality of contact areas.

13. A method of manufacturing an in-ear housing configured to be worn at least partly in an ear canal, comprising:
   using at least one of additive manufacturing or 3D printing to produce the in-ear housing, wherein:
      the manufactured in-ear housing comprises a plurality of contact areas configured in use to contact the ear canal and exert a radial pressure on the ear canal;
      the plurality of contact areas comprises a first contact area having a first texture pattern and a second contact area having a second texture pattern that is different than the first texture pattern; and
      the plurality of contact areas comprise at least one of: a greater roughness than at least a part of a remaining area of an outer surface of the in-ear housing; a greater friction properties/friction coefficient than the at least a part of the remaining area; a different material than the at least a part of the remaining area; a series of undulations; a plurality of surface structures; or granulations.

14. The method of claim 13, wherein the in-ear housing comprises at least one of an earmold or a part of a hearing device.

15. The method according to claim 14, wherein the in-ear housing is manufactured in accordance with a virtual design of the in-ear housing.

16. The method according to claim 15, wherein the virtual design of the in-ear housing includes at least one of a location of the plurality of contact areas or properties of the plurality of contact areas.

17. The method according to claim 15, wherein the virtual design is generated from a 3D model of the ear canal.

18. The method according to claim 15, further comprising:
   obtaining radial pressure calculations associated with the ear canal,
   wherein the virtual design is produced using the radial pressure calculations.

* * * * *